(12) United States Patent
Oba et al.

(10) Patent No.: US 11,390,837 B2
(45) Date of Patent: Jul. 19, 2022

(54) MICROCHANNEL DEVICE

(71) Applicant: FUJIFILM CORPORATION, Tokyo (JP)

(72) Inventors: Takahiro Oba, Kanagawa (JP); Akira Wakabayashi, Kanagawa (JP); Koju Ito, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 333 days.

(21) Appl. No.: 16/695,063

(22) Filed: Nov. 25, 2019

(65) Prior Publication Data
US 2020/0095527 A1    Mar. 26, 2020

Related U.S. Application Data

(63) Continuation of application No. PCT/JP2018/021931, filed on Jun. 7, 2018.

(30) Foreign Application Priority Data

Jun. 9, 2017 (JP) .............................. JP2017-114764

(51) Int. Cl.
*C12M 3/06* (2006.01)
*B81B 3/00* (2006.01)
*C12M 1/12* (2006.01)

(52) U.S. Cl.
CPC ........... *C12M 23/16* (2013.01); *B81B 3/0064* (2013.01); *C12M 25/02* (2013.01); *B81B 2203/0338* (2013.01)

(58) Field of Classification Search
None
See application file for complete search history.

(56) References Cited

U.S. PATENT DOCUMENTS

| 2009/0238722 A1 | 9/2009 | Mora-Fillat et al. |
| 2011/0171480 A1 | 7/2011 | Mori et al. |
| 2011/0250585 A1 | 10/2011 | Ingber et al. |

FOREIGN PATENT DOCUMENTS

| CN | 103058131 B | 9/2015 |
| CN | 105396633 A | 3/2016 |
| EP | 1975120 A2 | 10/2008 |
| JP | 2007-136280 A | 6/2007 |
| JP | 2008-246348 A | 10/2008 |
| JP | 2011-074140 A | 4/2011 |
| JP | 4945281 B2 | 6/2012 |
| JP | 2013-188677 A | 9/2013 |

(Continued)

OTHER PUBLICATIONS

English language translation of the following: Office Action dated Dec. 15, 2020, issued by the KIPO in corresponding Korean Patent Application No. 10-2019-7035230.

(Continued)

*Primary Examiner* — Lore R Jarrett
(74) *Attorney, Agent, or Firm* — Solaris Intellectual Property Group, PLLC

(57) ABSTRACT

A microchannel device includes: a channel unit which is configured of a plurality of channel members which are laminated in a thickness direction to define a microchannel, at least one of the channel members being made of a material having elasticity; and a holding member which is provided separately from or integrally with the channel unit and holds the channel unit in a state of being compressed in the thickness direction.

9 Claims, 7 Drawing Sheets

(56) References Cited

FOREIGN PATENT DOCUMENTS

| JP | 2013188677 A | 9/2013 |
|----|--------------|--------|
| JP | 5405374 B2   | 2/2014 |
| JP | 5415538 B2   | 2/2014 |
| JP | 5422230 B2   | 2/2014 |
| JP | 5700460 B2   | 4/2015 |
| JP | 5771962 B2   | 9/2015 |
| WO | 2010/032728 A1 | 3/2010 |

OTHER PUBLICATIONS

International Search Report issued in International Application No. PCT/JP2018/021931 dated Sep. 4, 2018.
Written Opinion of the ISA issued in International Application No. PCT/JP2018/021931 dated Sep. 4, 2018.
Office action dated Feb. 25, 2021 from the IPO in a Indian patent application No. 201947050210 corresponding to the instant patent application.
English language translation of the following: Office action dated Sep. 8, 2020 from the JPO in a Japanese patent application No. 2019-523980 corresponding to the instant patent application.
Extended European Search Report dated Mar. 26, 2020, issued in corresponding EP Patent Application No. 18812954.8.
Office action dated May 11, 2021 from the JPO in a Japanese patent application No. 2019-523980 corresponding to the instant patent application.
Office Action dated Oct. 20, 2021, issued by the CIPO in corresponding Canadian Patent Application No. 3,066,338.

MICROCHANNEL DEVICE

CROSS-REFERENCE TO RELATED APPLICATIONS

This application is a continuation application of International Application No. PCT/JP2018/021931, filed on Jun. 7, 2018, which is incorporated herein by reference in its entirety. Further, this application claims priority from Japanese Patent Application No. 2017-114764, filed on Jun. 9, 2017, the disclosure of which is incorporated by reference herein.

BACKGROUND

Technical Field

This disclosure relates to a microchannel device.

Related Art

A device having a channel with a width of a micrometer order, which is called a microchannel defined by a plurality of channel members, (hereinafter referred to as a "microchannel device") is known. For example, JP5700460B and JP5771962B disclose a cell culture device for culturing cells in a microchannel, or a configuration using a microchannel device as a microchannel chip. Further, JP5415538B discloses a configuration using a microchannel device as an organ mimic device having a micro flow path (microchannel).

In the cell culture device disclosed in JP5700460B, a pair of substrates as channel members which define a culture chamber as a microchannel is joined to each other by adsorption (self-adsorption). Further, in the microchannel chip disclosed in JP5771962B, three base materials as channel members which define a channel as a microchannel are joined to each other by a method such as anodic joining or pressure bonding.

Further, in the organ mimic device disclosed in JP5415538B, a pair of outer body portions as channel members which define a microchannel as a micro flow path is bonded to each other with an adhesive such as a bonding agent or an epoxy resin.

However, in a case where the channel members are joined to each other by bonding with an adhesive, there is a possibility that the adhesive component may flow into the microchannel and affect a solution, cells, or the like in the microchannel. Further, in a case where the channel members are joined to each other by pressure bonding or adsorption, the bonding strength between the channel members decreases, and thus there is a possibility that the required bonding strength may not be maintained.

SUMMARY

This disclosure provides, in view of the above facts, a microchannel device capable of suppressing a decrease in the bonding strength of a channel member and preventing an adhesive component from flowing into a microchannel.

A microchannel device according to a first aspect of this disclosure includes: a channel unit which is formed by a plurality of channel members which are laminated in a thickness direction to define a microchannel, at least one of the channel members being made of a material having elasticity; and a holding member which is provided separately from or integrally with the channel unit and holds the channel unit in a state of being compressed in the thickness direction.

According to the first aspect of this disclosure, the channel unit is held by the holding member, whereby the channel members configuring the channel unit are joined to each other. For this reason, in the microchannel device according to the first aspect, compared to a configuration in which the plurality of channel members configuring the channel unit are bonded to each other with an adhesive, an adhesive component can be prevented from flowing into the microchannel.

Further, at least one channel member of the channel members configuring the channel unit is made of a material having elasticity, and the channel unit is held in a state of being compressed in the thickness direction by the holding member. For this reason, in the microchannel device according to the first aspect, compared to a configuration in which the channel members are joined to each other by adsorption or pressure bonding, the bonding strength between the channel members can be increased.

In a second aspect of this disclosure, in the first aspect, the holding member may be a pair of holding plates provided at both ends in the thickness direction of the channel unit and having a plurality of bolt holes formed to penetrate in the thickness direction, and the pair of holding plates may be joined to each other by bolts respectively inserted into the bolt holes.

According to the second aspect of this disclosure, since the holding member consists of a pair of holding plates provided at both ends in the thickness direction of the channel unit, the channel member can be sandwiched between and held by the pair of holding plates. Further, the plurality of bolt holes are formed in the pair of holding plates, and the holding plates are joined to each other by a plurality of bolts inserted into the bolt holes. For this reason, in the microchannel device according to the second aspect, the holding plates can be easily joined to each other, and an adhesive component can be prevented from flowing into the microchannel, compared to a configuration in which the holding plates are bonded with an adhesive.

In a third aspect of this disclosure, in the first aspect, the holding member may be a pair of holding plates provided at both ends in the thickness direction of the channel unit, and the pair of holding plates may be joined to each other by locking a locking protrusion formed on one holding plate to a locked portion formed on the other holding plate.

According to the third aspect of this disclosure, the holding plates can be joined to each other by locking the locking protrusion formed on one holding plate to the locked portion formed on the other holding plate. For this reason, in the microchannel device according to the third aspect, it is possible to reduce a number of parts, compared to a configuration in which the holding plates are joined to each other with bolts.

In a fourth aspect of this disclosure, in the first aspect, the holding member may be a pair of holding plates provided at both ends in the thickness direction of the channel unit, and the pair of holding plates may be joined to each other by welding or bonding with an adhesive.

According to the fourth aspect of this disclosure, since the holding plates are joined to each other by welding or bonding, it is possible to reduce a number of parts. Further, in the microchannel device according to the fourth aspect, compared to a configuration in which the channel members are bonded to each other with an adhesive, an adhesive component can be suppressed from flowing into the microchannel.

In a fifth aspect of this disclosure, in the second to fourth aspects, the pair of holding plates may be provided separately from the channel unit and be sized to cover the entirety of both end faces in the thickness direction of the channel unit.

According to the fifth aspect of this disclosure, the holding plates are provided separately from the channel unit and sized to cover both end faces in the thickness direction of the channel unit. For this reason, in the microchannel device according to the fifth aspect, the entirety of the channel member made of a material having elasticity can be more uniformly compressed, and the bonding strength between the channel members can be further increased.

In a sixth aspect of this disclosure, in the second to fifth aspects, at least one spacer which defines an interval between the pair of holding plates may be provided around the channel unit between the pair of holding plates.

According to the sixth aspect of this disclosure, a spacer is provided between the holding plates. For this reason, in the microchannel device according to the sixth aspect, the interval between the holding plates can be defined by the spacer, and the entirety of the channel member made of a material having elasticity can be more uniformly compressed.

In a seventh aspect of this disclosure, in the first to sixth aspects, a porous membrane may be disposed between the channel members constituting the channel unit, and a deformation amount in the thickness direction of the channel unit after compression with respect to the channel unit before being sandwiched and compressed between the holding members may be larger than a thickness of the porous membrane and smaller than a height of the microchannel.

In general, in a case where a porous membrane is disposed between the channel members, it becomes particularly difficult to join the channel members to each other. Specifically, in a case where the channel members are bonded to each other with an adhesive, the adhesive easily flows into the microchannel through the porous membrane. Further, in a case where the channel members are joined to each other by adsorption or welding, there is a possibility that the porous membrane may be damaged.

Here, according to the seventh aspect of this disclosure, since the channel unit is compressed and held by the holding member, an adhesive can be prevented from flowing into the microchannel, and damage to the porous membrane can be suppressed. Further, in the microchannel device according to the seventh aspect, since the deformation amount in the thickness direction of the channel member is larger than the thickness of the porous membrane and smaller than the height of the microchannel, the microchannel can be suppressed from being compressed and blocked while suppressing formation of a gap around the porous membrane between the channel members.

In an eighth aspect of this disclosure, in the first to seventh aspects, the channel member made of a material having elasticity may have a rubber hardness by a type A durometer of JIS K6253, of 20 degrees or more and 80 degrees or less.

According to the eighth aspect of this disclosure, the channel member made of a material having elasticity has a rubber hardness by a type A durometer of JIS K6253, of 20 degrees or more and 80 degrees or less. For this reason, in the microchannel device according to the eighth aspect, compared to a case where the rubber hardness of the channel member is larger than 80 degrees, it is possible to increase the bonding strength between the channel members, and compared to a case where the rubber hardness of the channel member is smaller than 20 degrees, it is possible to suppress the microchannel from being compressed and deformed or blocked.

In a ninth aspect of this disclosure, in the first to eighth aspects, a deformation amount in the thickness direction of the channel unit may be 0.1 µm or more and 500 µm or less.

From the viewpoint of the bonding strength between the channel members, the deformation of the shape of the microchannel, and the like, the deformation amount in the thickness direction of the channel unit is suitably 0.1 µm or more and 500 µm or less.

In a tenth aspect of this disclosure, in the first to ninth aspects, the holding member may be a holding plate having a rubber hardness by a type A durometer of JIS K6253, of 80 degrees or more.

According to the tenth aspect of this disclosure, the holding member is a holding plate having a rubber hardness by a type A durometer of JIS K6253, of 80 degrees or more. For this reason, in the microchannel device according to the tenth aspect, compared to a case where the rubber hardness of the holding plate is smaller than 80 degrees, the compression of the channel member in the thickness direction can be performed more effectively, and the bonding strength between the channel members can be increased.

According to the above aspects, the microchannel device of this disclosure can suppress a decrease in the bonding strength of the channel member and prevent the adhesive component from flowing into the microchannel.

DESCRIPTION OF EMBODIMENTS

Figure 1:
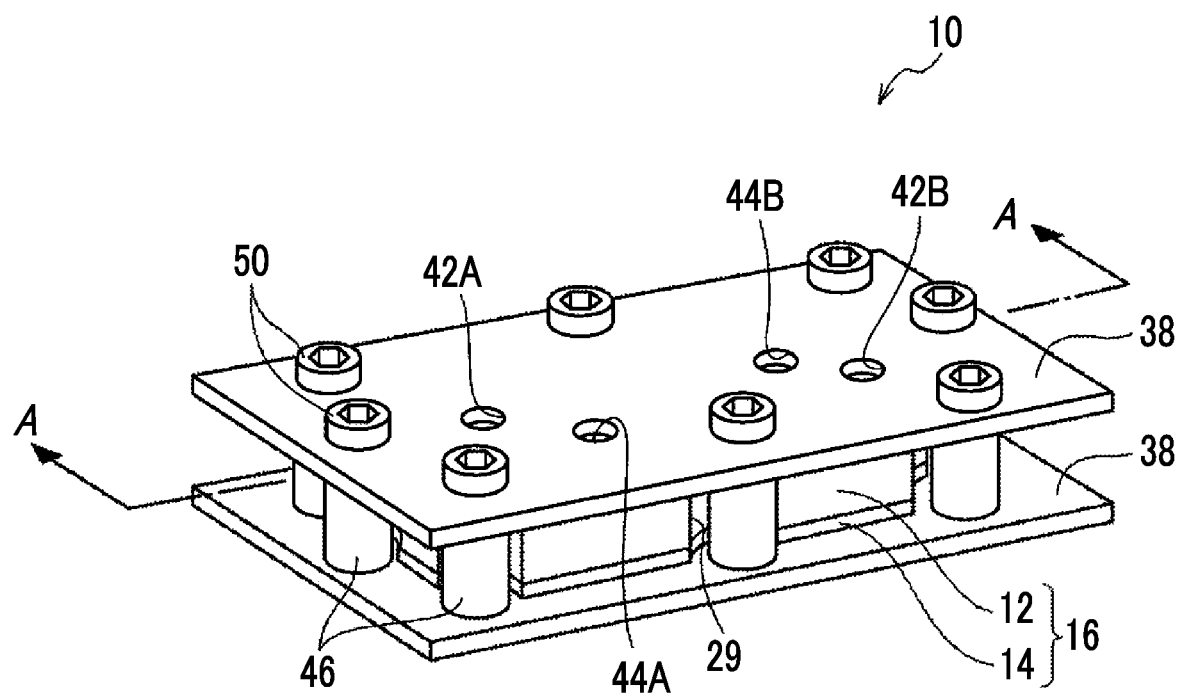
FIG. 1 is a perspective view showing an overall structure of a microchannel device in an exemplary embodiment.

Hereinafter, an example of an exemplary embodiment of this disclosure will be described using FIGS. 1 to 10. The following exemplary embodiment is to illustrate this disclosure and is not intended to limit the scope of this disclosure. Further, in order to facilitate the description of each configuration, the dimensions of each configuration in the drawings are appropriately changed. For this reason, the scale in the drawings is different from the actual scale.

<Channel Unit>

Figure 2:
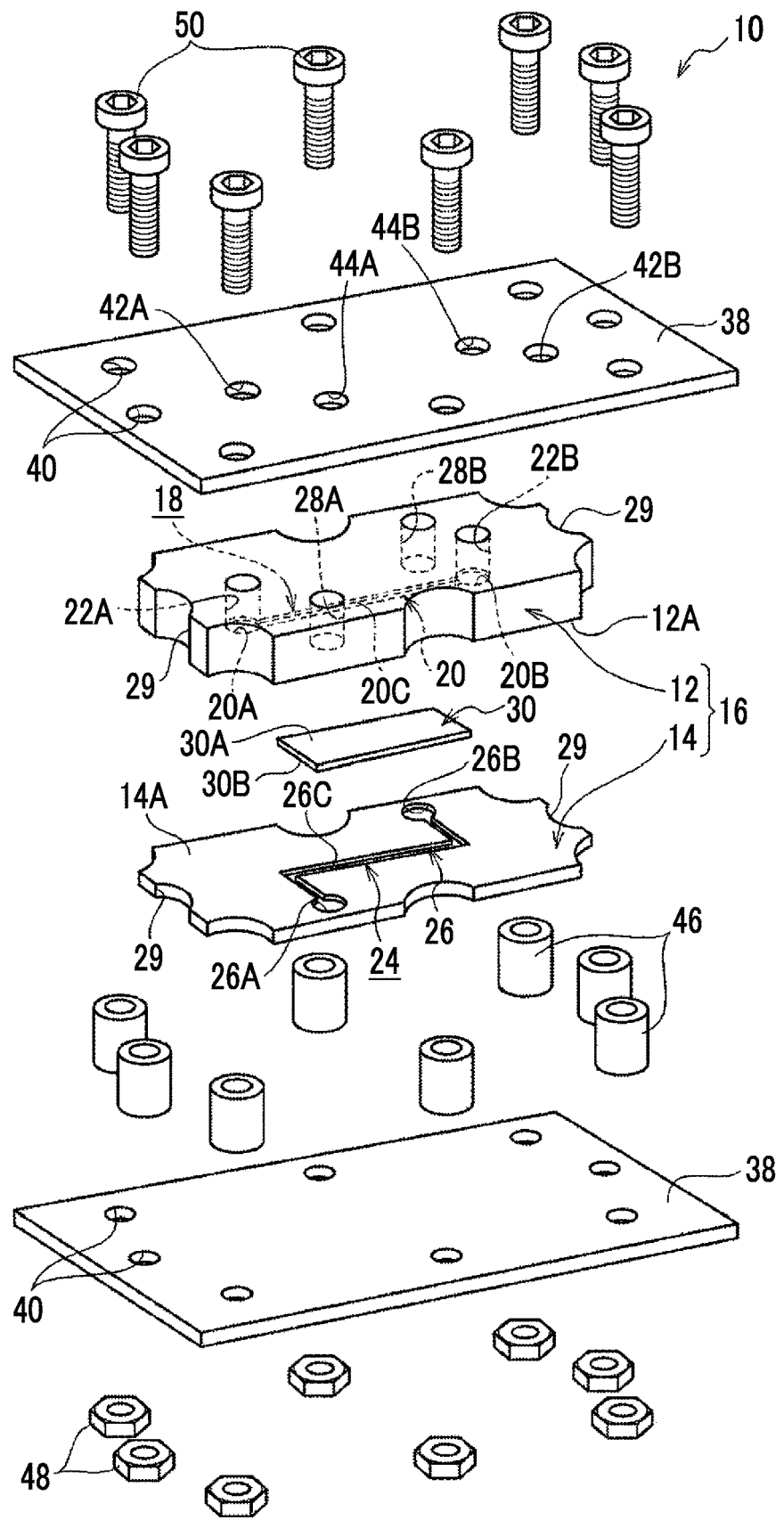
FIG. 2 is an exploded perspective view showing the overall structure of the microchannel device in the exemplary embodiment.

As shown in FIGS. 1 and 2, a microchannel device 10 of this exemplary embodiment has a channel unit 16 configured of an upper channel member 12 and a lower channel member 14 laminated in a thickness direction. It is preferable that each of the upper channel member 12 and the lower channel member 14 is made of a transparent material having elasticity, such as PDMS (polydimethylsiloxane) as an example.

As the material configuring the upper channel member 12 and the lower channel member 14, in addition to PDMS (polydimethylsiloxane), epoxy resin, urethane resin, styrene thermoplastic elastomer, olefin thermoplastic elastomer, acrylic thermoplastic elastomer, polyvinyl alcohol, or the like can be given as an example.

Here, the upper channel member 12 and the lower channel member 14 have a rubber hardness of preferably 20 degrees or more and 80 degrees or less and more preferably 50 degrees or more and 70 degrees or less. The "rubber hardness" can be evaluated by measuring the hardness of each of the upper channel member 12 and the lower channel member 14 by a type A durometer with a method defined in JIS K6253: 2012.

As shown in FIG. 2, a recessed portion 20 which defines an upper microchannel 18 is formed on the lower surface of the upper channel member 12, that is, a surface 12A facing the lower channel member 14. The recessed portion 20 has an inflow port 20A, an outflow port 20B, and a channel portion 20C which makes the inflow port 20A and the outflow port 20B communicate with each other. Further, through-holes 22A and 22B which penetrate the upper channel member 12 in the thickness direction and have lower ends communicating with the inflow port 20A and the outflow port 20B are formed in the upper channel member 12.

Similarly, a recessed portion 26 which defines a lower microchannel 24 is formed on the upper surface of the lower channel member 14, that is, a surface 14A facing the upper channel member 12. The recessed portion 26 has an inflow port 26A, an outflow port 26B, and a channel portion 26C which makes the inflow port 26A and the outflow port 26B communicate with each other.

Here, the inflow port 26A and the outflow port 26B of the lower channel member 14 are provided at positions which do not overlap the inflow port 20A and the outflow port 20B of the upper channel member 12 when viewed in a plan view. On the other hand, the channel portion 26C of the lower channel member 14 is provided at a position overlapping the channel portion 20C of the upper channel member 12 when viewed in a plan view.

Further, through-holes 28A and 28B which penetrate the upper channel member 12 in the thickness direction and have lower ends communicating with the inflow port 26A and the outflow port 26B of the lower channel member 14 are formed in the upper channel member 12. Further, a recessed portion 29 is provided at a position where a spacer 46 (described later) is disposed, on the outer peripheral surface of the channel unit 16 (each of the outer peripheral surface of each of the upper channel member 12 and the lower channel member 14).

<Porous Membrane>

A porous membrane 30 is disposed between the facing surfaces 12A and 14A of the upper channel member 12 and the lower channel member 14. The porous membrane 30 is made of a hydrophobic polymer which can be dissolved in a hydrophobic organic solvent, as an example. The hydrophobic organic solvent is a liquid having a solubility in water of 25° C. of 10 (g/100 g water) or less.

As the hydrophobic polymer, a polymer such as polystyrene, polyacrylate, polymethacrylate, polyacrylamide, polymethacrylamide, polyvinyl chloride, polyvinylidene chloride, polyvinylidene fluoride, polyhexafluoropropene, polyvinyl ether, polyvinyl carbazole, polyvinyl acetate, polytetrafluoroethylene, polyester (for example, polyethylene terephthalate, polyethylene naphthalate, polyethylene succinate, polybutylene succinate, polylactic acid, poly-3-hydroxybutyrate, or the like), polylactone (for example, polycaprolactone or the like), polyamide or polyimide (for example, nylon, polyamic acid, or the like), polyurethane, polyurea, polybutadiene, polycarbonate, polyaromatics, polysulfone, polyethersulfone, polysiloxane derivatives, cellulose acylate (for example, triacetyl cellulose, cellulose acetate propionate, or cellulose acetate butyrate) can be given as an example.

These polymers may be homopolymers, copolymers, polymer blends, or polymer alloys, as necessary, from the viewpoint of solubility in solvents, optical physical properties, electrical physical properties, membrane strength, elasticity, and the like. Further, these polymers may be used alone or in combination of two or more. The material of the porous membrane 30 is not limited to a hydrophobic polymer, and various materials can be selected from the viewpoint of adhesive properties of a cell, or the like.

An upper surface 30A and a lower surface 30B (hereinafter, there is a case where the upper surface 30A and the lower surface 30B are collectively referred to as a principal surface) of the porous membrane 30 are sized to substantially cover the channel portions 20C and 26C of the upper microchannel 18 and the lower microchannel 24, and separates the upper microchannel 18 and the lower microchannel 24 from each other.

Specifically, the upper surface 30A of the porous membrane 30, that is, the principal surface facing the upper channel member 12 defines the upper microchannel 18 together with the recessed portion 20 of the upper channel member 12, and the lower surface 30B of the porous membrane 30, that is, the principal surface facing the lower channel member 14 defines the lower microchannel 24 together with the recessed portion 26 of the lower channel member 14.

Figure 3:
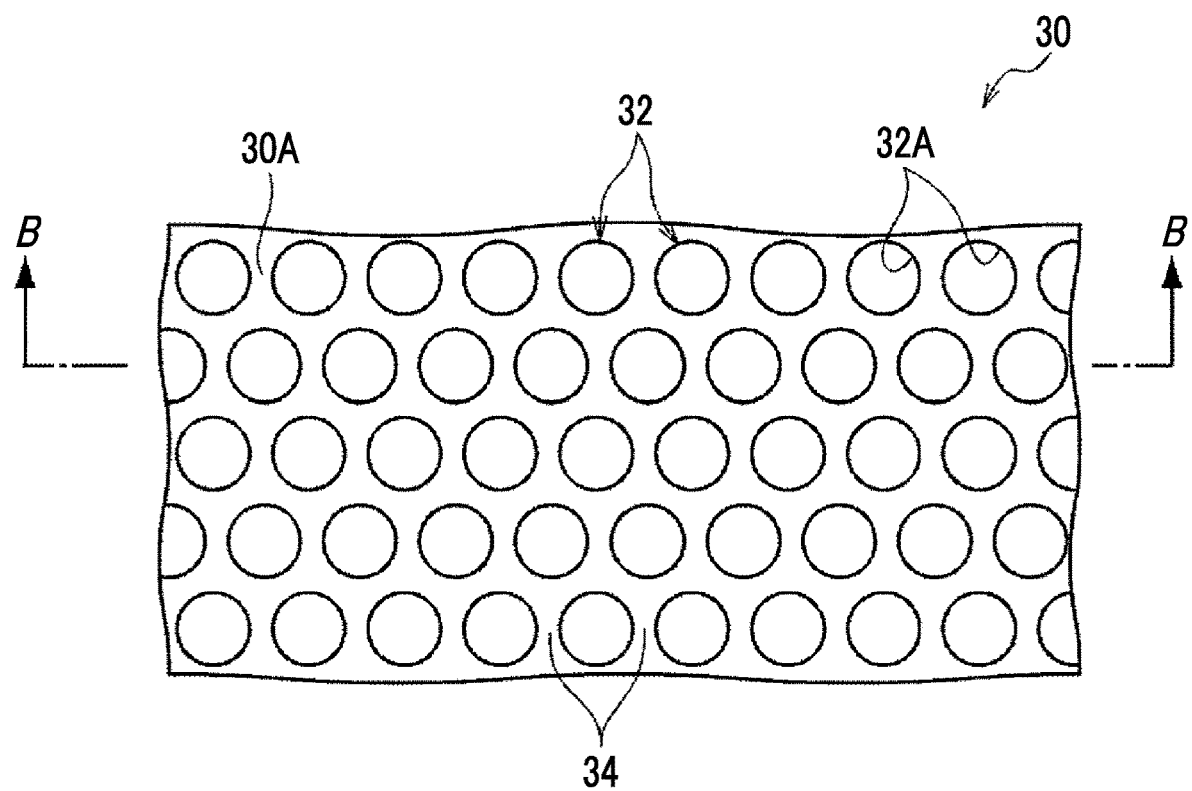
FIG. 3 is a plan view showing a porous membrane of the microchannel device in the exemplary embodiment.
Figure 4:
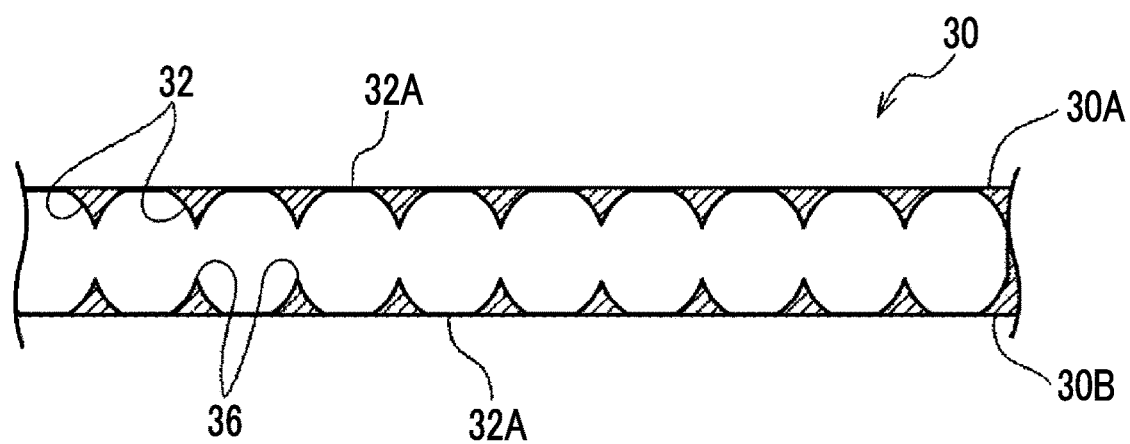
FIG. 4 is a cross-sectional view taken along line B-B in FIG. 3.

As shown in FIGS. 3 and 4, a plurality of through-holes 32 penetrating in the thickness direction are formed in the porous membrane 30, and openings 32A of the through-holes 32 are provided on each of the upper surface 30A and the lower surface 30B of the porous membrane 30. Further, as shown in FIG. 3, the opening 32A has a circular shape when viewed in a plan view. The openings 32A are provided to be spaced from each other, and a flat portion 34 extends between the openings 32A adjacent to each other. The opening 32A is not limited to a circular shape and may have a polygonal shape or an elliptical shape.

The plurality of openings 32A are regularly disposed, and in this exemplary embodiment, the openings 32A are disposed in a honeycomb shape as an example. The disposition in the honeycomb shape is disposition in which a parallel hexagon (preferably a regular hexagon) or a shape close thereto is set as a unit and the center of the opening 32A is located at the vertex and the intersection of the diagonal lines of the figure. Here, the "center of the opening" means the center of the opening 32A when viewed in a plan view.

The disposition of the openings 32A is not limited to a honeycomb shape and may be disposition in a lattice shape or a face-centered lattice shape. The disposition in the lattice shape is disposition in which a parallelogram (needless to say, a square, a rectangle, and a rhombus are included. Preferably a square) or a shape close thereto is set as a unit and the center of the opening 32A is located at the vertex of the figure. The disposition in the face-centered lattice shape is disposition in which a parallelogram (needless to say, a square, a rectangle, and a rhombus are included. Preferably a square) or a shape close thereto is set as a unit and the center of the opening is located at the vertex and the intersection of the diagonal lines of the figure.

As shown in FIG. 4, the through-hole 32 of the porous membrane 30 has a spherical segment shape with the upper end and lower end of a sphere cut off. Further, the through-holes 32 adjacent to each other communicate with each other through a communication hole 36 in the interior of the porous membrane 30.

It is preferable that one through-hole 32 is in communication with all the through-holes 32 adjacent thereto, and as in this exemplary embodiment, in a case where the openings 32A of the plurality of through-holes 32 are disposed in a honeycomb shape, one through-hole 32 is in communication with six through-holes 32 adjacent thereto through six communication holes 36, respectively. The through-hole 32 may have a barrel shape, a columnar shape, a polygonal column shape, or the like, and the communication hole 36 may be a tubular void which connects the through-holes 32 adjacent to each other.

In a case where the microchannel device 10 of this exemplary embodiment is used as a cell culture device or the like, it is preferable that a region where cells on at least the principal surface of the porous membrane 30 are seeded is coated with at least one selected from the group consisting of fibronectin, collagen (for example, I-type collagen, IV-type collagen, or V-type collagen), laminin, vitronectin, gelatin, perlecan, nidogen, proteoglycan, osteopontin, tenascin, nephronectin, basement membrane matrix, and polylysine. By coating the porous membrane 30, it becomes possible to increase the adhesive properties of cells.

Further, in a case where the microchannel device 10 of this exemplary embodiment is used as an organ mimic device or the like, it is preferable that a cell layer configuring an organ to be mimicked is provided on the principal surface of the porous membrane 30. By providing the cell layer on the principal surface of the porous membrane 30, it becomes possible to make the inside of the upper microchannel 18 and the inside of the lower microchannel 24 an environment close to inside of the organ to be mimicked.

As a method of manufacturing the porous membrane 30 with the through-holes 32 formed therein, in addition to a nanoprint method or a dew condensation method, an etching method, a sand blast method, or a method such as press forming can be given as an example. The nanoprint method is a method of manufacturing the through-hole 32 by pouring a material configuring the porous membrane 30 into a die having a concavo-convex shape, or pressing a die against a material configuring the porous membrane 30. Further, the dew condensation method is a method of forming the through-holes 32 by causing dew to be formed on the surface of a material configuring the porous membrane 30 and using water droplets as dies.

In the dew condensation method, compared to other methods, it is possible to reduce the thickness of the porous membrane 30, it is possible to increase a void volume or an opening ratio of the opening 32A, and it is possible to provide the communication hole 36 in the porous membrane 30. For this reason, in this exemplary embodiment, the porous membrane 30 is manufactured by the dew condensation method. Details of the dew condensation method are described in, for example, JP4945281B, JP5422230B, JP2011-074140A, and JP5405374B.

<Holding Member>

As shown in FIGS. 1 and 2, the microchannel device 10 has a pair of holding plates 38 as holding members for holding the channel unit 16 in a state of being compressed in the thickness direction. The pair of holding plates 38 is provided separately from the channel unit 16 at both ends in the thickness direction of the channel unit 16, that is, on the upper side of the upper channel member 12 and the lower side of the lower channel member 14, and is sized to cover the entire upper surface of the upper channel member 12 and the entire lower surface of the lower channel member 14, respectively.

It is preferable that the holding plate 38 is made of a hard and transparent polymer material. Therefore, as the constituent material of the holding plate 38, a cycloolefin polymer, acrylic, polycarbonate, polystyrene, polyethylene terephthalate, or the like can be given as an example. Further, it is preferable that the holding plate 38 is harder than the upper channel member 12 and the lower channel member 14, and the rubber hardness thereof is preferably 80 degrees or more, and more preferably 90 degrees or more.

As shown in FIG. 2, a plurality of (in this exemplary embodiment, eight) bolt holes 40 penetrating in the thickness direction are respectively formed at positions corresponding to each other, of the pair of holding plates 38. Further, through-holes 42A, 42B, 44A, and 44B respectively communicating with the through-holes 22A, 22B, 28A, and 28B of the upper channel member 12 are formed in the holding plate 38 provided on the upper side of the upper channel member 12.

A tube (not shown) is connected to each of the through-holes 42A, 42B, 44A, and 44B, and a solution, a cell suspension, or the like flows into the upper microchannel 18 and the lower microchannel 24 and flows out from the upper microchannel 18 and the lower microchannel 24 through the tubes.

A plurality of (in this exemplary embodiment, eight) spacers 46 which define the interval between the holding plates 38 are respectively provided outside the recessed portions 29 of the channel unit 16 between the pair of holding plates 38. The spacer 46 is a cylindrical member having an inner diameter that is substantially the same as the inner diameter of the bolt hole 40, and is disposed at a position corresponding to each of the bolt holes 40.

The pair of holding plates 38 are joined to each other by a plurality of bolts 50 that are inserted into the bolt holes 40 and the spacers 46 and fixed by nuts 48. At this time, the upper channel member 12 and the lower channel member 14 are compressed and held by the pair of holding plates 38 in a state where the porous membrane 30 is sandwiched therebetween.

Figure 5:
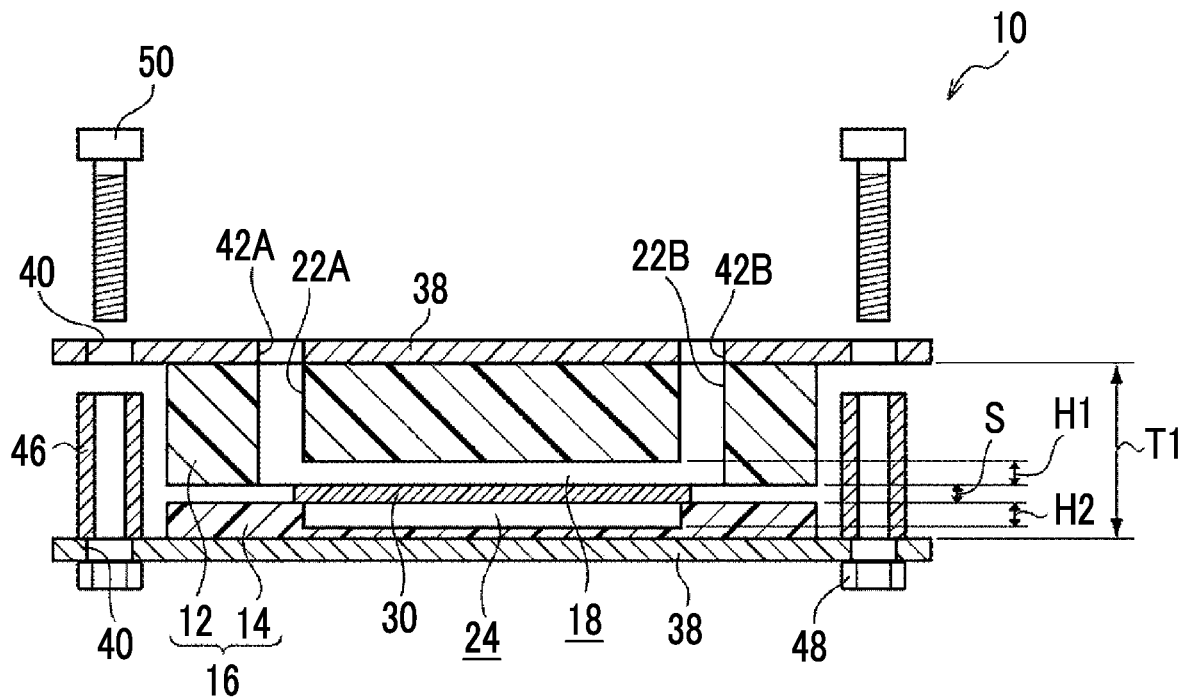
FIG. 5 is a cross-sectional view taken along line A-A in FIG. 1, showing the microchannel device before a channel unit is compressed.
Figure 6:
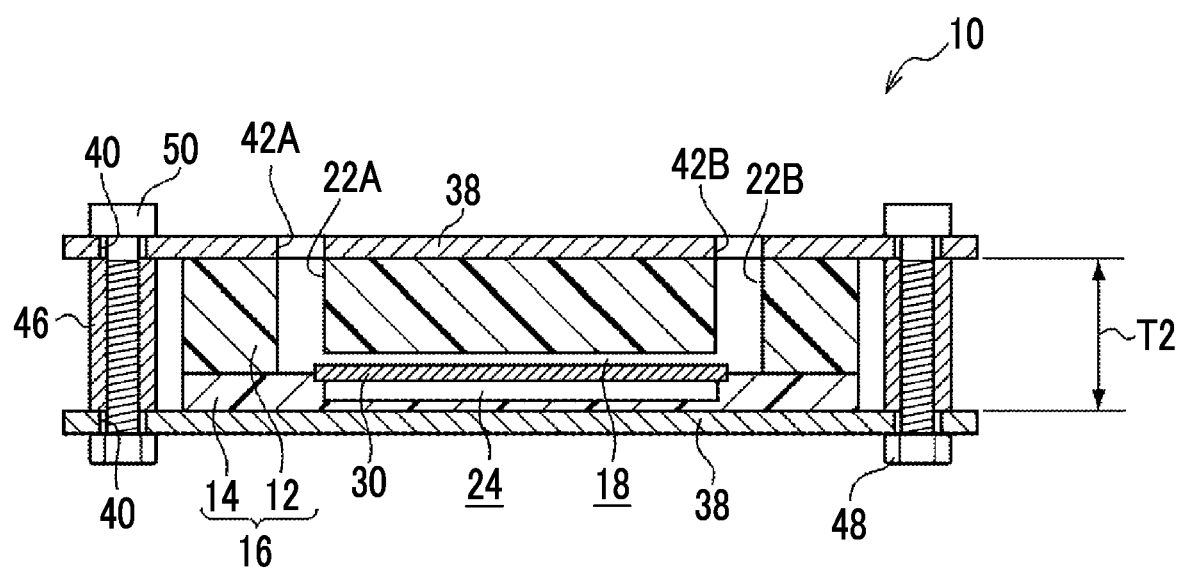
FIG. 6 is a cross-sectional view taken along line A-A in FIG. 1, showing the microchannel device after the channel unit is compressed.

Specifically, as shown in FIGS. 5 and 6, the channel unit 16 is sandwiched and compressed between the pair of holding plates 38, whereby the thickness of the channel unit 16 is changed (deformed) from a thickness T1 thicker than the height of the spacer 46 to a thickness T2 which is the same thickness as the height of the spacer 46.

Here, it is preferable that the deformation amount T1-T2 in the thickness direction of the channel unit 16 is larger than a thickness S of the porous membrane 30 and smaller than each of a height H1 of the upper microchannel 18 and a height H2 of the lower microchannel 24.

More specifically, from the viewpoint of the bonding strength between the upper channel member 12 and the lower channel member 14, the deformation of the shape of the upper microchannel 18 and the lower microchannel 24, and the like, it is preferable that the deformation amount T1-T2 in the thickness direction of the channel unit 16 is 0.1 μm or more and 500 μm or less. Further, it is more preferable that the deformation amount T1-T2 in the thickness direction of the channel unit 16 is 1 μm or more and 50 μm or less. The thickness T1 of the channel unit 16 is, for example, in a range of about 0.5 mm to 20 mm.

<Method of Manufacturing Microchannel Device>

Figure 7:
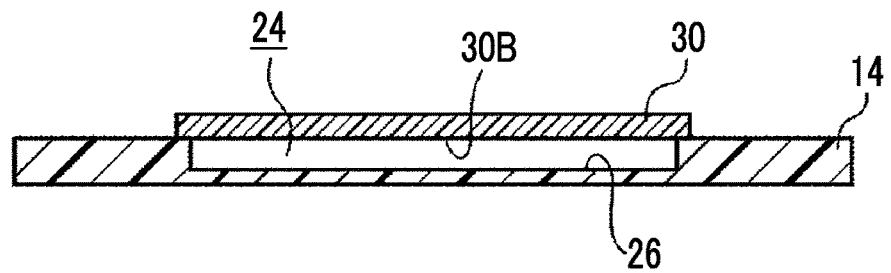
FIG. 7 is a cross-sectional view showing a manufacturing process of the microchannel device in the exemplary embodiment.

In order to manufacture the microchannel device 10 of this exemplary embodiment, first, the porous membrane 30 having sterilized paper attached to the principal surface thereof is prepared. Then, the sterilized paper on the lower surface 30B of the porous membrane 30 is peeled off by tweezers, and as shown in FIG. 7, the porous membrane 30 is placed on the lower channel member 14 with the recessed portion 26 formed therein, and the porous membrane 30 and the lower channel member 14 is joined. In this way, the lower microchannel 24 is defined by the recessed portion 26 of the lower channel member 14 and the porous membrane 30.

Figure 8:
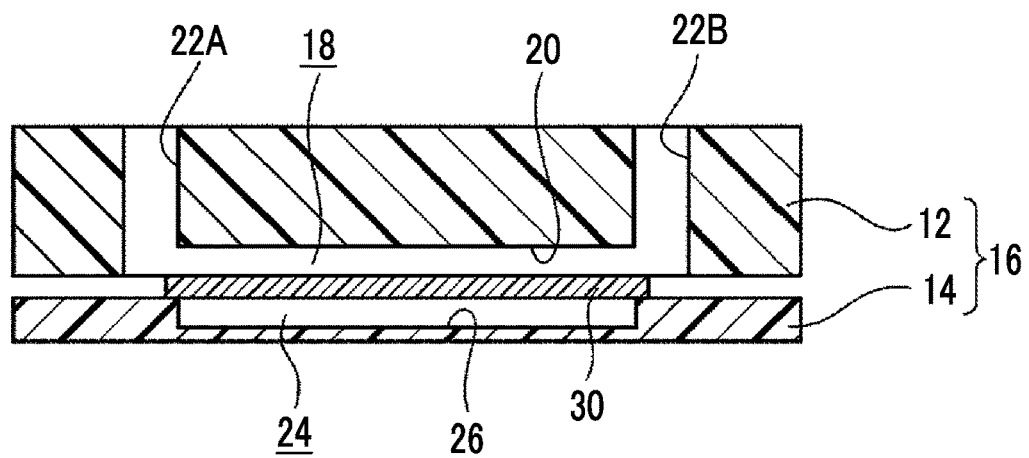
FIG. 8 is a cross-sectional view showing a manufacturing process of the microchannel device in the exemplary embodiment.

Next, the sterilized paper on the upper surface 30A of the porous membrane 30 is peeled off by tweezers, and the positions of the upper channel member 12 and the lower channel member 14 are aligned with each other while confirming a microscope, and thus as shown in FIG. 8, the upper channel member 12 with the recessed portion 20 formed therein is laminated on the porous membrane 30. In this way, the upper microchannel 18 is defined by the recessed portion 20 of the upper channel member 12 and the porous membrane 30.

Figure 9:
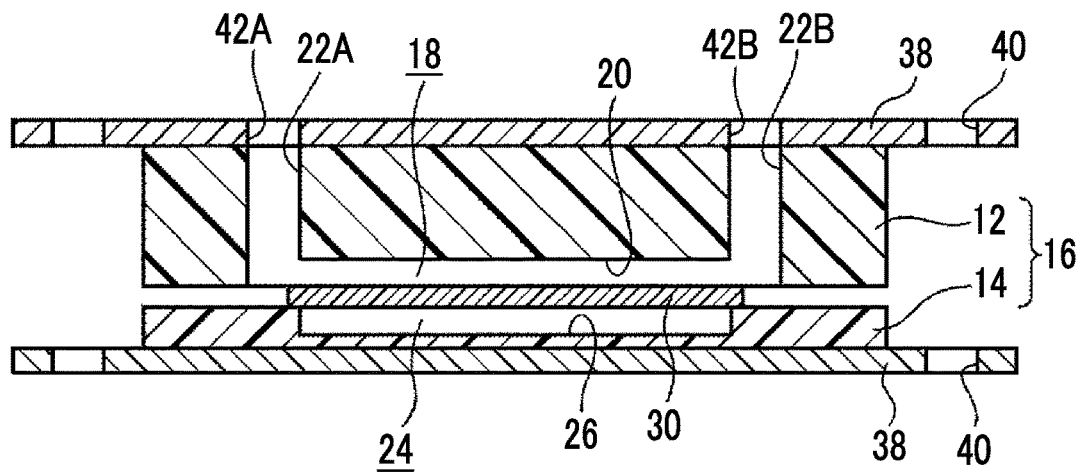
FIG. 9 is a cross-sectional view showing a manufacturing process of the microchannel device in the exemplary embodiment.

Next, as shown in FIG. 9, the holding plate 38 is placed on the upper surface of the upper channel member 12 while aligning the positions of the through-holes 22A, 22B, 42A, and 42B with each other. Thereafter, the channel unit 16 is turned over, and the holding plate 38 is placed on the lower surface of the lower channel member 14.

Figure 10:
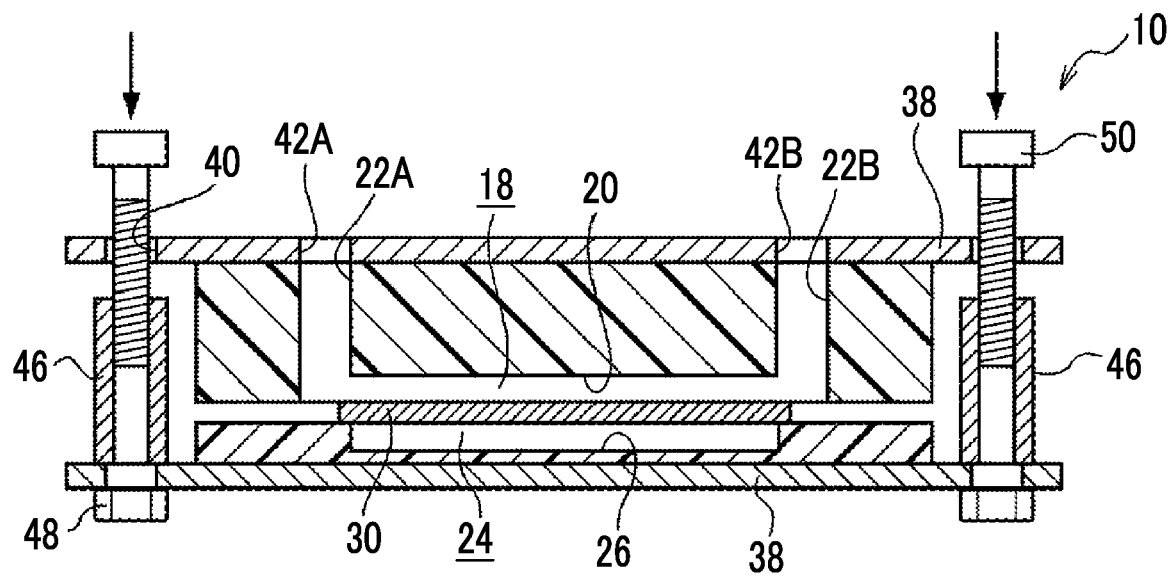
FIG. 10 is a cross-sectional view showing a manufacturing process of the microchannel device in the exemplary embodiment.

Next, as shown in FIG. 10, the microchannel device 10 is manufactured by disposing the spacers 46 around the channel unit 16 and fastening the holding plates 38 to each other with the bolts 50 and the nuts 48. The manufacturing process described above is an example, and the order may be changed. Further, other processes may be added to the process described above.

According to this exemplary embodiment, the upper channel member 12 and the lower channel member 14 configuring the channel unit 16 are sandwiched between the pair of holding plates 38 that are separate from the channel unit 16, and the holding plates 38 are joined to each other by the bolts 50, whereby the upper microchannel 18 and the lower microchannel 24 are joined.

For this reason, the holding plates 38 can be easily joined, and compared to a configuration in which the upper channel member 12 and the lower channel member 14 are bonded to each other with an adhesive, the adhesive component can be prevented from flowing into the upper microchannel 18 and the lower microchannel 24.

Further, the upper channel member 12 and the lower channel member 14 configuring the channel unit 16 are made of a material having elasticity and held in a state of being compressed in the thickness direction by the holding plates 38. For this reason, compared to a configuration in which the upper channel member 12 and the lower channel member 14 are joined by adsorption or pressure bonding, the bonding strength between the upper channel member 12 and the lower channel member 14 can be increased.

Further, according to this exemplary embodiment, the holding plate 38 is sized to cover each of the entire upper surface of the upper channel member 12 and the entire lower surface of the lower channel member 14. Further, the plurality of spacers 46 that define the interval between the holding plates 38 are provided between the holding plates 38. For this reason, the whole of the upper channel member 12 and the whole of the lower channel member 14 can be compressed uniformly, and the bonding strength between upper channel member 12 and lower channel member 14 can be increased.

Further, in general, in a case where the porous membrane 30 is disposed between the upper channel member 12 and the lower channel member 14, it becomes particularly difficult to join the upper channel member 12 and the lower channel member 14. Specifically, in a case where the upper channel member 12 and the lower channel member 14 are bonded to each other with an adhesive, the adhesive easily flows into the upper microchannel 18 and the lower microchannel 24 through the porous membrane 30. Further, in a case where the upper channel member 12 and the lower channel member 14 are joined by adsorption or welding, there is a possibility that the porous membrane 30 may be damaged.

Here, according to this exemplary embodiment, since the channel unit 16 is compressed and held by the holding plates 38, the adhesive can be prevented from flowing into the upper microchannel 18 and the lower microchannel 24, and damage to the porous membrane 30 can be suppressed.

Further, the deformation amount T1-T2 in the thickness direction of the channel unit 16 is larger than the thickness S of the porous membrane 30 and smaller than the height H1 of the upper microchannel 18 and the height H2 of the lower microchannel 24. For this reason, the upper microchannel 18 and the lower microchannel 24 can be suppressed from being compressed and blocked while suppressing formation of a gap around the porous membrane 30 between the upper channel member 12 and the lower channel member 14.

In particular, in this exemplary embodiment, the rubber hardness of each of the upper channel member 12 and the lower channel member 14 is set to be 20 degrees or more and 80 degrees or less. For this reason, compared to a case where the rubber hardness of each of the upper channel member 12 and the lower channel member 14 is larger than 80 degrees, it is possible to further increase the bonding strength between the upper channel member 12 and the lower channel member 14. Further, compared to a case where the rubber hardness of each of the upper channel member 12 and the lower channel member 14 is smaller than 20 degrees, it is possible to further suppress the upper microchannel 18 and the lower microchannel 24 from being compressed and deformed or blocked.

Other Exemplary Embodiments

An example of the exemplary embodiment of this disclosure has been described above. However, this disclosure is not limited to the above, and in addition to the above, various modifications can be implemented within a scope which does not depart from the gist of this disclosure.

In the exemplary embodiment described above, the microchannel device 10 comprises the upper microchannel 18 and the lower microchannel 24 which are separated by the porous membrane 30, and the channel unit 16 is configured of the upper channel member 12 and the lower channel member 14 made of a material having elasticity. However, the microchannel device 10 may not have the porous membrane 30, and it is sufficient that at least one channel member of the channel members configuring the channel unit 16 is made of a material having elasticity.

Figure 11:
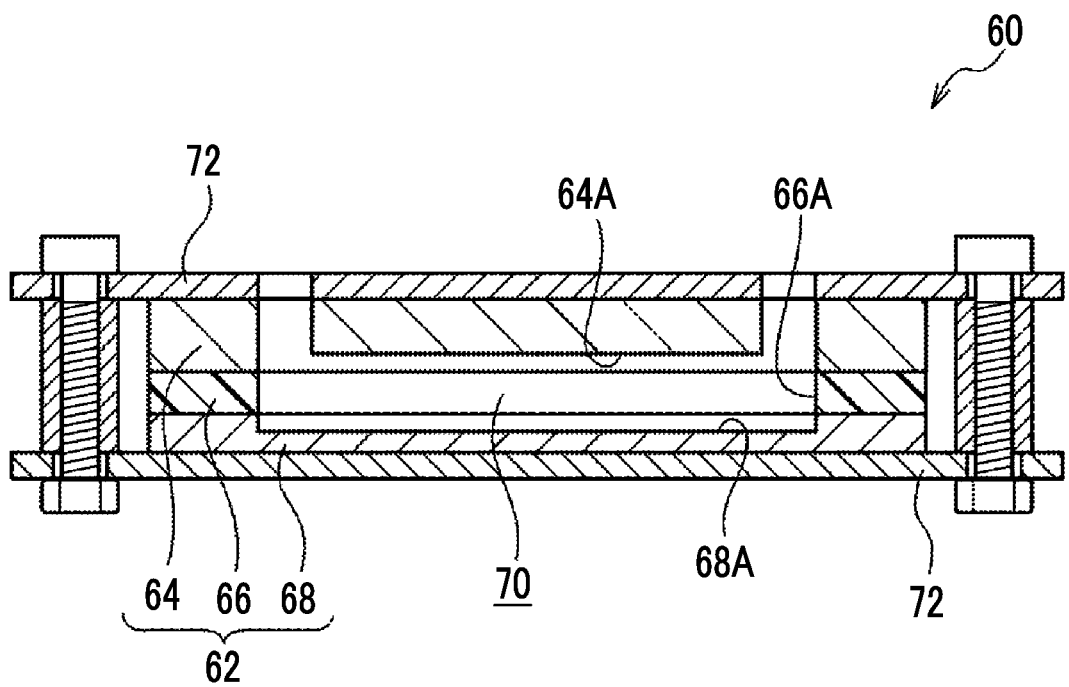
FIG. 11 is a cross-sectional view showing a microchannel device in a modification example.

Specifically, as shown in FIG. 11, a channel unit 62 of a microchannel device 60 may be configured of three channel members; an upper channel member 64, an intermediate channel member 66, and a lower channel member 68 which are laminated in the thickness direction.

Here, the upper channel member 64 and the lower channel member 68 are made of an inelastic material, and only the intermediate channel member 66 is made of a material having elasticity. Further, one microchannel 70 is defined by a recessed portion 64A formed on the lower surface of the upper channel member 64, a through-hole 66A formed in the intermediate channel member 66, and a recessed portion 68A formed on the upper surface of the lower channel member 68.

Other configurations of the microchannel device 60 are the same as those of the microchannel device 10. In the microchannel device 60 shown in FIG. 11, the intermediate channel member 66 is compressed in the thickness direction by sandwiching the channel unit 62 between a pair of holding plates 72, and thus the upper channel member 64, the intermediate channel member 66, and the lower channel member 68 can be joined to each other.

Further, in the exemplary embodiment described above, the pair of holding plates 38 joined to each other by the bolts 50 is used as a holding member. However, it is sufficient that the holding member is configured to be capable of holding at least the channel unit 16 in a state of being compressed in the thickness direction.

Figure 12:
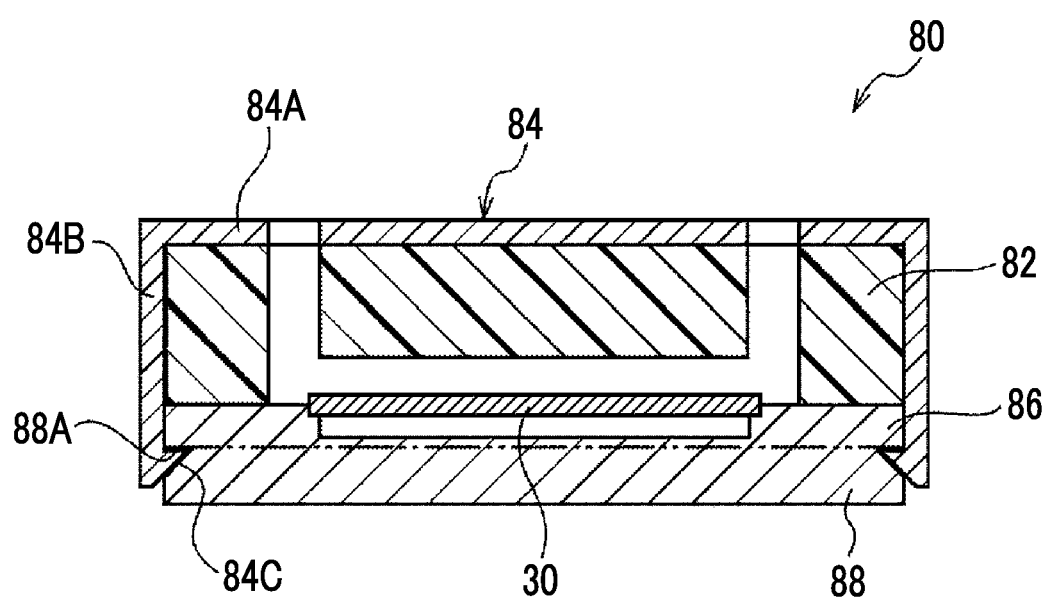
FIG. 12 is a cross-sectional view showing a microchannel device in a modification example.

Specifically, as shown in FIG. 12, a holding member of a microchannel device 80 may have an upper holding plate 84 provided separately from the upper channel member 82 on the upper side of the upper channel member 82, and a lower holding plate 88 provided integrally with a lower channel member 86. The upper channel member 82 is made of a material having elasticity, and the lower channel member 86 is made of an inelastic material.

Here, the upper holding plate 84 has a principal surface portion 84A sized to cover the entire upper surface of the upper channel member 82, a hanging portion 84B extending downward from an outer peripheral portion of the principal surface portion 84A, and a locking protrusion 84C protruding inward from a lower end of the hanging portion 84B. On the other hand, a recessed portion 88A as a locked portion is formed on the outer peripheral surface of the lower holding plate 88. Other configurations of the microchannel device 80 are the same as those of the microchannel device 10.

In the microchannel device 80 shown in FIG. 12, the upper holding plate 84 and the lower holding plate 88 are joined to each other by locking the locking protrusion 84C formed on the upper holding plate 84 to the recessed portion 88A formed on the lower holding plate 88, in a state where the upper channel member 82 is sandwiched therebetween. For this reason, compared to a configuration in which the upper holding plate 84 and the lower holding plate 88 are joined with bolts, a number of parts can be reduced.

In addition, in the exemplary embodiment described above, the pair of holding plates 38 may be joined to each other by welding or bonding with an adhesive. In this case, compared to a configuration in which the holding plates 38 are joined by the bolts 50, the number of parts can be reduced. Further, compared to a configuration in which the upper channel member 12 and the lower channel member 14 are bonded to each other with an adhesive, the adhesive component can be suppressed from flowing into the upper microchannel 18 and the lower microchannel 24.

Further, in the exemplary embodiment described above, the plurality of spacers 46 are provided between the holding plates 38. However, it is sufficient that at least one spacer 46 is provided, and for example, a single annular spacer having through-holes respectively formed at positions corresponding to the bolt holes 40 may be provided between the holding plates 38.

The entirety of the disclosure of Japanese Patent Application No. 2017-114764 is incorporated herein by reference.

All literatures, patent applications, and technical standards mentioned in this specification are incorporated in this specification by reference to the same extent as in a case where individual literature, patent application, and technical standard are specifically and individually incorporated by reference.

What is claimed is:

1. A microchannel device comprising:
    a channel unit that includes an upper channel member and a lower channel member, which are laminated in a thickness direction to define a microchannel, at least one of the upper channel member or the lower channel member being made of a material having elasticity; and
    a pair of holding plates provided at both ends, in the thickness direction, of the channel unit,
    wherein a porous membrane is disposed between the upper channel member and the lower channel member that constitute the channel unit, and
    wherein the pair of holding plates hold the channel unit in a state of being compressed in the thickness direction, such that a deformation amount in the thickness direction of the channel unit after compression, with respect to the channel unit before compression by the pair of holding plates, is larger than a thickness of the porous membrane and smaller than a height of the microchannel.

2. The microchannel device according to claim 1, wherein each of the pair of holding plates includes a plurality of bolt holes formed to penetrate in the thickness direction, and
    the pair of holding plates are joined to each other by bolts respectively inserted into the bolt holes.

3. The microchannel device according to claim 2, wherein the pair of holding plates are not integral with the channel unit and are sized to cover the entirety of both end faces, in the thickness direction, of the channel unit.

4. The microchannel device according to claim 2, wherein at least one spacer which defines an interval between the pair of holding plates is provided around the channel unit between the pair of holding plates.

5. The microchannel device according to claim 1, wherein the pair of holding plates are joined to each other by locking a locking protrusion formed on one holding plate to a locked portion formed on the other holding plate.

6. The microchannel device according to claim 1, wherein the pair of holding plates are welded to each other or are joined to each other with an adhesive.

7. The microchannel device according to claim 1, wherein the material having elasticity has a rubber hardness by a type A durometer of JIS K6253, of from 20 degrees to 80 degrees.

8. The microchannel device according to claim 1, wherein the deformation amount, in the thickness direction, of the channel unit, in the state of being compressed by the holding plates, is from 0.1 μm to 500 μm.

9. The microchannel device according to claim 1, wherein each of the pair of holding plates is a holding plate having a rubber hardness by a type A durometer of JIS K6253, of 80 degrees or more.

* * * * *